United States Patent [19] [11] Patent Number: 6,097,297
Fard [45] Date of Patent: Aug. 1, 2000

[54] WETNESS AWARENESS TRAINING DEVICE

[76] Inventor: Safieh Bahramian Fard, 22 Rock Rose, Irvine, Calif. 92612

[21] Appl. No.: 09/322,310

[22] Filed: May 28, 1999

Related U.S. Application Data

[63] Continuation-in-part of application No. 08/969,372, May 28, 1998, abandoned.

[51] Int. Cl.⁷ ..................................................... G08B 21/00
[52] U.S. Cl. ........................ 340/604; 340/573.5; 340/605; 128/886; 604/361
[58] Field of Search ..................................... 340/602, 603, 340/604, 605, 573.5; 128/886; 604/361

[56] References Cited

U.S. PATENT DOCUMENTS

| | | |
|---|---|---|
| 4,704,108 | 11/1987 | Okada et al. . |
| 4,754,264 | 6/1988 | Okada et al. . |
| 4,800,370 | 1/1989 | Vetecnik . |
| 5,008,964 | 4/1991 | Dean et al. . |
| 5,264,830 | 11/1993 | Kline et al. . |
| 5,291,181 | 3/1994 | DePonte . |
| 5,392,032 | 2/1995 | Kline et al. . |
| 5,395,358 | 3/1995 | Lu . |
| 5,459,452 | 10/1995 | De Ponte . |
| 5,469,145 | 11/1995 | Johnson . |
| 5,469,146 | 11/1995 | Gurler . |
| 5,537,695 | 7/1996 | Ander . |
| 5,557,263 | 9/1996 | Fisher et al. ............................. 740/605 |
| 5,570,082 | 10/1996 | Mahgerefteh et al. . |
| 5,790,036 | 8/1998 | Fisher et al. . |
| 5,817,076 | 10/1998 | Fard . |
| 5,868,723 | 2/1999 | Al-Sabah .............................. 340/573.5 |
| 5,903,222 | 5/1999 | Kawarizadeh et al. .................. 340/604 |

Primary Examiner—Edward Lefkowitz
Attorney, Agent, or Firm—Curtis L. Harrington

[57] ABSTRACT

A moisture detection system (11) of the invention provides a disposable wicked dual electrode strip as a sensor wick and conductor assembly (31) which can be used in conjunction with any type of diaper or garment. The dual electrode strip includes two conductive strips (41, 43) which have a wick located in contact with the conductive strips. Even a small amount of urine is absorbed by the wick and distributed between the conductive strips to quickly change the resistance between the strips. A detector/transmitter (35) engages the sensor wick and conductor assembly (31), and can use the sensor wick and conductor assembly (31) as a transmitting antenna for increased range at low power, to alert a receiver (13) carried by a care giver.

13 Claims, 7 Drawing Sheets

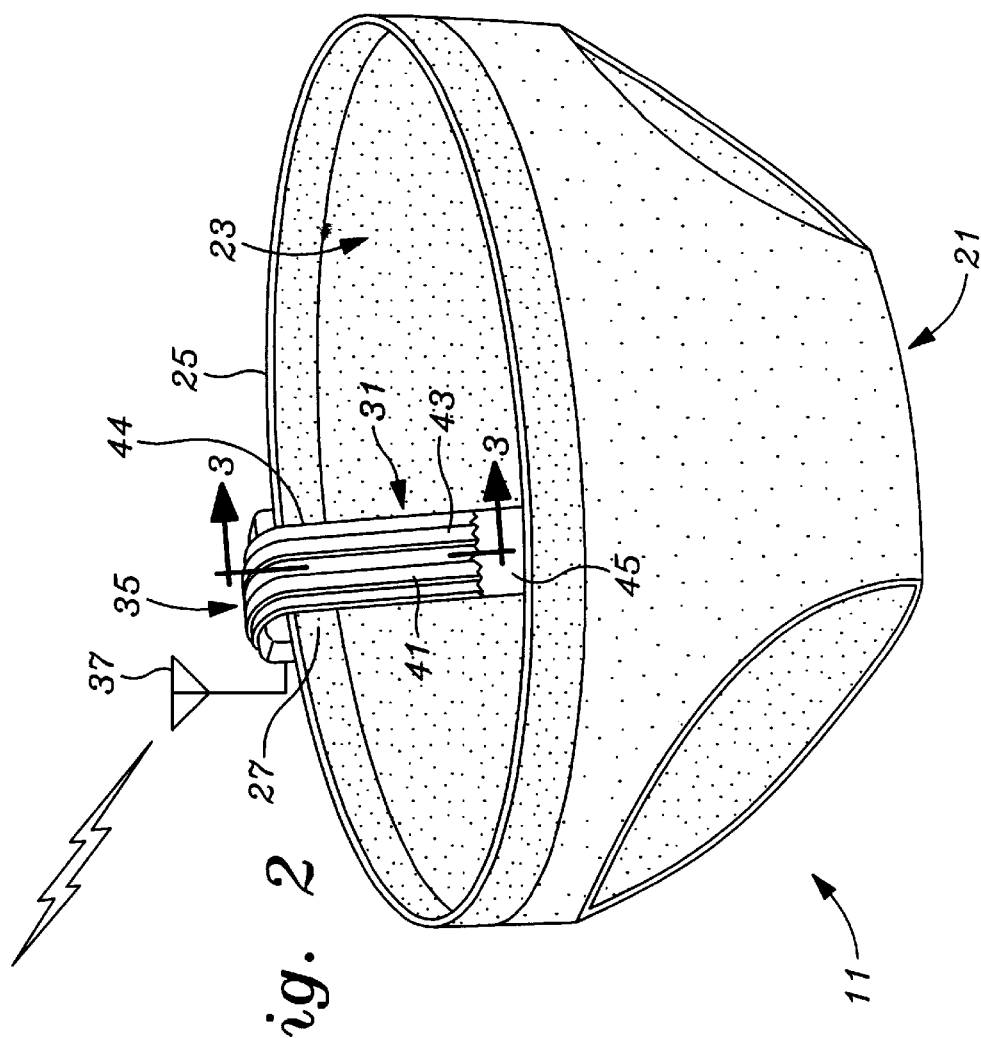
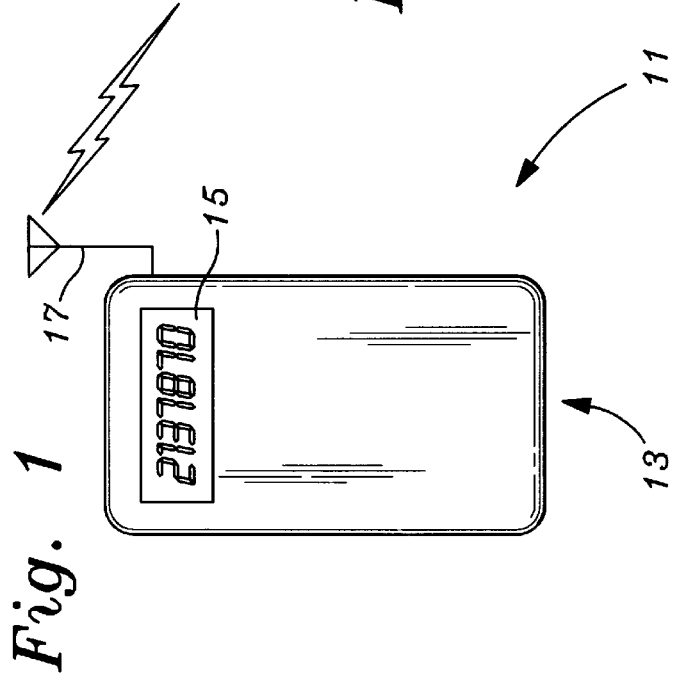

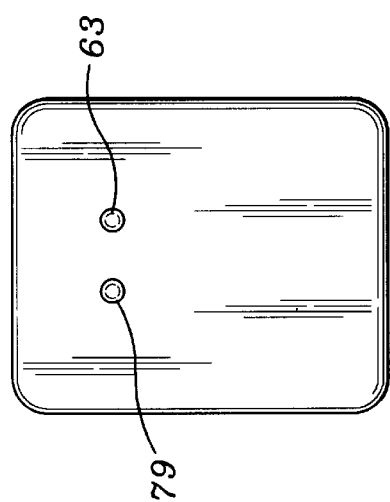
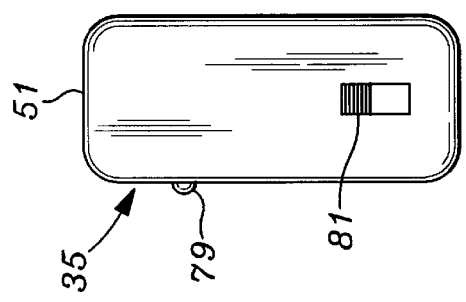
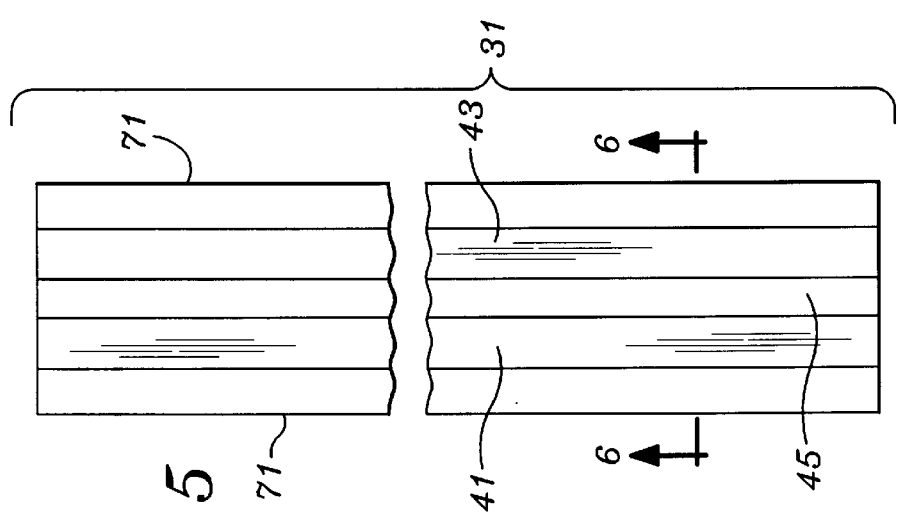
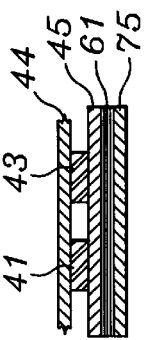
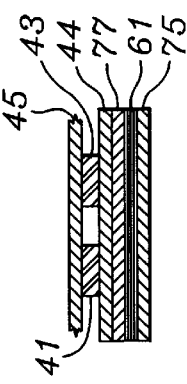
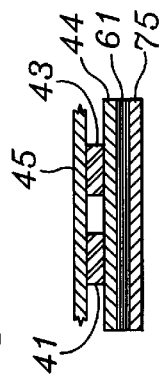

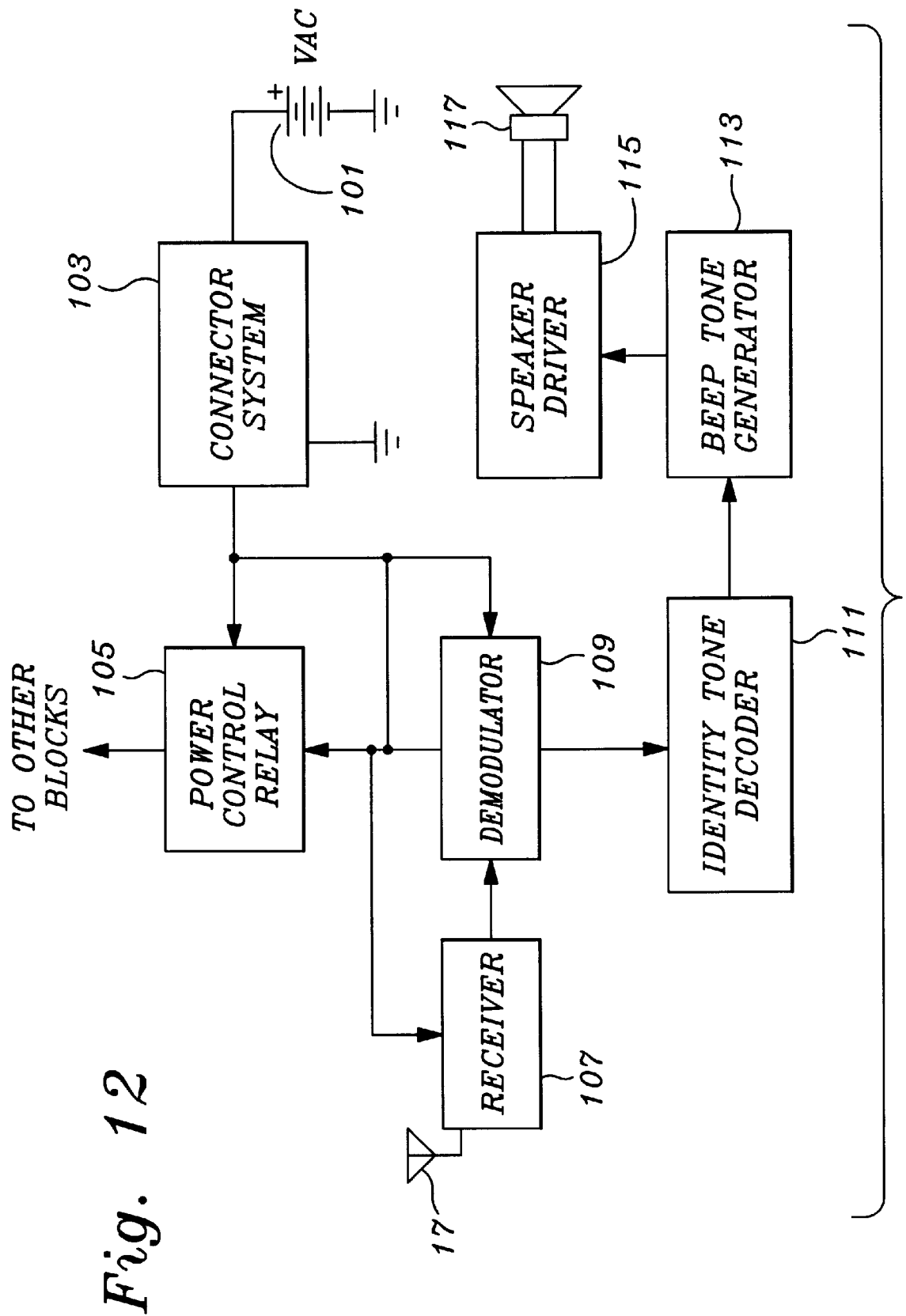

WETNESS AWARENESS TRAINING DEVICE

This is a Continuation-in-Part of U.S. patent application Ser. No. 08/969,372 filed May 28, 1998.

FIELD OF THE INVENTION

The present invention relates to a flexible wetness awareness system which enables user selection of personal garments, yet providing safe and effective moisture detection by the use of a user install able wicking system with a mounting device transmitter and user carried receiver.

BACKGROUND OF THE INVENTION

It is desirable for care givers of individual children to change wet diapers as soon as possible for a variety of reasons. Hygiene, avoidance of diaper rash, and containing the moisture contents are but a few reasons. In institutional settings where one care giver is responsible for larger numbers of diapered children, the ability to alert the care giver of a child with a wet diaper enables the care giver to better manage their time, as well as to enable them to avoid tactile checking of each child's diapers. Tactile checking is preferably performed with the care giver washing hands between the time that each child's diaper is checked. The time involved usually prevents this proper procedure. Where this procedure is not followed, germs from one child are passed to the other children as the checking progresses.

Several solutions to the above problem have been proposed, but none have gained wide acceptance. U.S. Pat. No. 5,570,082 to Mahgerefteh et al, uses an electromagnetic field large enough that the presence of water in the urine couples the field to react with a non linear element to create harmonics which are detected by a receiver within the device creating the field. The device in essence uses a powerful transceiver to blast an electromagnetic signal at a child's diaper containing an antenna system. Wetting on the antenna changes its natural re-radiating frequency so that the receiver of the transceiver picks up a shifted frequency which is re-radiated from a transmitter antenna within the diaper on which the child wets. Subsequent science has shown that where the body is exposed to electromagnetic radiation, the weaker the power and the less frequent the duty cycle, the better it is.

U.S. Pat. No. 5,291,181 discloses a multiple circuit resistance triggered electrode system within a diaper, connected to an individualized transmitter and then to a nurses station. The contact is made using a large rectangular flexible sheet of material which uncomfortably fits within the diaper.

U.S. Pat. No. 5,395,358 discloses a pointed device, having a blade and which cuts into a diaper to detect moisture. Once moisture is detected, music is played to draw attention to the wet diaper.

U.S. Pat. No. 5,264,830 discloses snaps which connect a device surrounded by a cushioning housing. The device outputs an audible alarm. The circuit uses the interruption of an oscillator to trigger the alarm.

U.S. Pat. No. 4,704,108 to Okada et al discloses a diaper having a water permeable inner sheet, water absorber and water impermeable outer sheet. Metal layers are formed on opposite sides of the water impermeable sheet at the time the diaper is formed. A wicking layer of tissue paper is taught to be disposed between a water content sensing layer and an outer layer. Since the metal conductors are oppositely disposed, wetness in contact with one conductor must be present sufficiently to flow around an impermeable layer to contact the second electrode on the back side of the impermeable layer. The problem with this design is that a large amount of urine is necessary in order to trigger a metal sensor which is custom built into a diaper. Where the child urinates only a little, or where the child is lying on its side, the design of Okada will probably not trigger. Where the object is to keep the child as dry as possible, or to prevent re-inflammation of diaper rash, the Okada design will fail.

In addition, the above sensor structure designs are built into custom made diapers at the time the diaper is manufactured. This will drive up the cost for the diapers considerably given that the conductive or resonant structure will need to be built into and match a given brand of sensor circuit. Shelf space storage increases and the unit cost rises. Where specialty diapers have to be constructed, the additional built in value combines with the shelf space occupied to prohibitively increase the price and decrease availability.

U.S. Patent to Fisher et al., discloses a bed wetting device having sharp alligator clips which attach a large plastic carrier loosely to the adult's pants. The assembly includes a layer with oppositely disposed conductors and a complex carrier and attachment assembly which would be completely unsafe and inappropriate for children. The interchange ability and disposability combined are awkward and do not facilitate quick changeability as would be experienced in diaper changing.

The above set forth structures also fail in their attempt to provide a physical separation of the measurement conductors to prevent shorting out with movement and wear, and also fail to provide a more sensitive indicator of moisture.

Given that diapers are already available in cloth and paper versions which vary greatly in quality and construction and given that the product and product channels are already established, what is needed is a system for wetness monitoring which utilizes the existing market products and quality array. If pre-existing diapers can be utilized, the manufacturing cost can be reduced and the diapers themselves will present only a competitive cost item in the system.

What is needed is a wetness sensor which is easy to construct and which will alert a care provider even if only a small amount of urine is present. The care giver should be notified without a noise near the child which would be startling. The ideal alert system will be a transmitter which is modest in both transmit power and duration to avoid adverse affects on the child's body. The transmitter should ideally operate by short pulses of low duty cycle, and battery conservation should be important.

SUMMARY OF THE INVENTION

The moisture detection system of the invention provides a disposable wicked dual electrode strip which can be used in conjunction with any type of diaper. The dual electrode strip includes two conductive strips which have a wick located in contact with the conductive strips. Even a small amount of urine is absorbed by the wick and distributed between the conductive strips to quickly change the resistance between the strips.

Overall requirements include safety and comfort for the child as a primary consideration. Other considerations include manufacturing cost as a primary consideration to insure that the system of the invention is widely available and utilizable. The system of the invention includes minimum size components to maximize use. The system has ruggedness and reliability and low power consumption in all modes.

A battery is preferably a 3 volt lithium watch type for high transmitting voltage and long life to provide a small physical size while maintaining sufficient battery life and wide commercial availability. The system provides a battery cover which is splash and water-proof. The battery connectors are rugged to withstand a mild to medium level of abuse and polarized where possible to eliminate the necessity for reverse battery error. The sensor and transmitter preferably adds minimum thickness to the overall diaper dimensions and provides that the battery cover can be part of the connector.

To conserve power, it is preferably that only the continuity detector be connected continuously to the battery. A relay controls power to functional portions of the circuit to extend the life of the battery during the more predominant extended periods of a"dry" condition, but when urine moisture is detected, power is delivered to all circuits. The detection and transmitter circuit ideally causes only a minimum voltage drop in the battery, which even initially is a safe, low 3 volts.

A continuity detector signals the presence of moisture in the wick material between the conductors and is not mistriggered by insignificant moisture in the wick, as by sweat or humidity. The circuit draws low or no current during the "dry" wick condition and only minimal current through the wick conductor electrodes during moist wick conditions for both safety and long battery life. A moist wick condition enables all circuits.

A sound generator is preferably located in a receiver but in some variation may be located at the child's diaper so long as a tone is not loud and may alert, but not reward or alarm the child. Whether at the detector or receiver, the tone should not create excessive current drain and the tone may range from a simple beep to a more complex tone if a microcomputer chip is used in the design, and may be selected to match the efficiency of a given speaker. The circuit ideally includes a speaker driver to amplify the sound generator tone to create sufficient loudness by the speaker at low current drain, and will facilitate the match of electrical characteristics of the speaker. The speaker driver creates low quiescent current during operation to minimize current drain. The size of the speaker should be sufficient for proper sound output, exposed to the air for audio energy transfer, yet splash and moisture proof. A preferable speaker will enable a complex tone to be used.

A transmitter is preferably within FCC regulations for frequency and power with sufficient transmission range and signal reliability. The frequency and power should be selected with component cost and antenna complexity and availability in mind. The transmitter should be a pulsed transmitter with a low duty cycle to extend battery life, and with sufficient transmission at 3 volts of input power. Pulse modulation by an identity tone may be used to increase reliability of signal and enable identification of the particular transmitter which is transmitting. The frequency should be stable over the life of the battery to enable reliable reception.

A modulator controls amplitude, frequency or both of the transmitter output power. The modulator should enable power consumption of the transmitter during short pulses of the low duty cycle pulse oscillator. The transmitter signal is shaped by modulator to create a signal which is unique and readily recognized by the receiver.

Techniques to create an identifiable signal may include pulse code modulation, an identity tone generator or frequency hopping. The selected technique should enable the receiver to recognize the signal while the receiver rejects other false signals it may receive. Microchip programming would enable a number of unique tones, codes or frequency output sets to be easily stored and generated as needed.

The length and orientation of the conductive electrode sensors can enable one or both of the conductive electrodes to perform double duty as a transmitting antenna, to eliminate the need for an additional length of antenna conductor. The use of the conductive electrode sensors as an antenna can be accomplished without affecting the operation of the continuity detector since continuity can be measured with direct current, whereas the antenna transmission is an alternating current characteristic.

A wicking electrode structure is easy to construct with as low of a cost possible associated with the connector which attaches to the conductors of the wicking structure. The connection is safe and comfortable for the child and the connector, detector and transmitter module should be easy to clean.

The sensor wick and conductor assembly is comfortable, clean and is constructed to meets sterility regulations for diaper use. The conductors are rugged but are child safe should the child come into possession of them. The conductor structure are so inexpensive that they can and should be disposed with the soiled diaper. The sensor wick and conductor assembly does not trigger the continuity detector for insignificant moisture conditions. The sensor wick and conductor assembly is ideally self adhesive and may have a weak adhesive to enable the sensor wick and conductor assembly to be easily removed without residue, especially where re-usable cotton diapers are the diapers of choice for use with the system of the invention.

The receiver of the invention carried by the care provider is sensitive enough to receive a transmitter signal at a significant distance from the child wearing the sensor/transmitter, diaper and sensor wick and conductor assembly. The frequencies at which the transmitter and receiver operate may be selectable using switches on both, especially where different surroundings, buildings, dividers and the like may operate to negatively affect the signal. The receiver is constantly powered, whereas the transmitter only powers up upon an indication from the continuity detector circuit that urine moisture is present. The demodulator of the receiver separates the modulated portion of the signal from the carrier received and is also constantly powered.

Ideally the receiver antenna is contained within the receiver housing in order to minimize chances for breakage and to facilitate easy carriage by the care provider. The length of the antenna will be naturally reducible at higher frequencies and may take the form of a single or multiple wire loop around the inside of a pager sized case.

The invention provides a wetness detection and signaling system that is so firmly affixed to the diaper that it will not be dislodged and/or disabled by the subject trainee. The system of the invention provides a wetness detection and signaling system that remains clean and can be easily transferred from a used diaper to a clean diaper. The system of the invention provides a wetness detection and signaling system that does not in any way interfere with the functioning of the diaper. The system of the invention provides a wetness detection and signaling system whose transmitter incorporates a miniature battery having adequate life, while also having sufficient transmission range to allow the caretaker normal mobility. The invention provides a system that incorporates a small transmitter on the diaper that signals a remote receiver carried by the caretaker, without any other intermediary components such as remote energy sources or radio signal repeaters. A wetness detection Wick which is appropriately sensitive to the condition of wetness in the diaper that is caused by the act of urination, and is insensitive to other insignificant amounts of moisture that are often found in the diaper environment. A wetness detector wick assembly, or sensor wick and conductor assembly, is comprised of a thin wick layer that is fabricated with a inner layer of moisture absorbing pad material, covered by a moisture passing membrane on one side, and coated with an adhesive on the other side. Within the moisture absorbing pad are positioned flexible conductors that serve as the electrodes of a electrical resistance measuring device. In addition, the electrodes in the sensor wick and conductor assembly can serve as an transmitting antenna for the radio frequency transmitter that is connected to the sensor wick and conductor assembly. The sensor wick and conductor assembly is self-adhesive and is attached to the inner surface of a disposable, or re-useable diaper. The sensor wick and conductor assembly extends past the top edge of the diaper, folds over that edge, overlaps the device known as the sensor/transmitter, and is attached to the outer surface of the diaper. The electrodes embedded in the sensor wick and conductor assembly contact electrical terminals mounted on the surface of the sensor/transmitter.

The inventive system provides a complete system for the enhancement of the WAT training process by the immediate detection of the act of urination in the diaper. Also, the inventive system provides a system that applies to current WAT methods and current diapering methods and materials. The consumer is allowed to use any commercially available diaper with the WAT system. The system that does not require custom manufactured and costly diapers. The system provide a wetness detector sensor wick and conductor assembly whose sensitivity can easily be adjusted by minor changes to the configuration during manufacture. The inventive system also provides a wetness detector sensor wick and conductor assembly whose sensitivity has been adjusted to reliably detect the act of urination without being mis-triggered by insignificant amounts of moisture in the diaper, and which insures complete cleanliness of the wetness sensor wick and conductor assembly. The inventive system provides a wetness detector Wick that can be used with any commercially available diaper, and alerts the caretaker immediately upon the act of urination. Yet another aspect of the inventive system is to provide a signaling system that properly alerts the subject trainee immediately upon the act of urination, and to provide a wetness detection and signaling system that is attached only to the diaper and provides complete freedom of movement and comfort for the subject trainee. Still another advantage of the invention is to provide a wetness detection and signaling system that is attached only to the diaper and provides complete safety for the subject trainee, and to provide a wetness detection and signaling system that is sufficiently large and firmly affixed to the diaper to present no choke or other hazards to the subject trainee.

Upon urination, the conductivity between the conductors of the sensor wick and conductor assembly increases. When the level of conductivity exceeds a preset level, the sensor/transmitter initiates the signaling of the baby and caretaker. The sensitivity to moisture of the moisture detection system is affected by several factors, and the sensitivity can therefore be changed by the adjustment of these factors. One of the factors that affects sensitivity is the physical spacing between the electrodes of the sensor wick and conductor assembly. The more closely spaced, the greater the likelihood that a small amount of moisture will be distributed in the Wick such that a conductive path between electrodes will be established. The more widely spaced, the more moisture needs to be present in the sensor wick and conductor assembly to establish that conductive path. Another factor affecting sensitivity to moisture is the physical characteristics of the absorbent pad. The less absorbent the pad, the more a single drop of moisture will spread and provide a conductive path between electrodes. This absorbency is affected by both the absorbency factor of the material, and the quantity of that material. Another factor affecting sensitivity to moisture is the conductivity threshold level of the sensor/transmitter. The sensor has a continuity detector measures the amount of conductivity between the electrodes, and when the continuity exceeds a preset level the urination signals are initiated. By changing the continuity detection threshold, the sensitivity to moisture is adjusted. Therefore, by making adjustments to the combined factors noted above, the designer can adjust the moisture detection system to signal the act of urination without being mis-triggered by small amounts of moisture. Due to the construction of the sensor wick and conductor assembly, urine that is directed at the Wick cannot flow through the Wick to be absorbed by the diaper. Because of this, it may be desirable for the width of the sensor wick and conductor assembly to be as narrow as possible so that the urine can easily flow around it. A variation of the sensor wick and conductor assembly is constructed with a permeable backing sheet 1 so that the urine can flow through the Wick to the diaper where it can be absorbed. In this configuration a backing sheet is flexible and tear-resistant, but permeable so that urine can flow through the wick to be absorbed by the diaper. An adhesive coating is applied to the backing sheet in a low density pattern, so that the adhesive coating does not impede the flow of urine. An antenna Coupler routes the detection current from the sensor wick and conductor assembly to the detector/transmitter. Upon sensing the wetness condition, the continuity detector of the sensor/transmitter enables the Power Control. When enabled, the Power Control applies power to all circuitry of the Transmitter. Only the continuity detector of the sensor/transmitter will preferably have power continuously applied, all other blocks are switchably disconnected from battery power during dry diaper conditions to extend battery life. Also, upon sensing the wetness condition, the Continuity Detector enables the Sound Generator which sends a beep tone to a speaker driver which drives an optional speaker on the sensor/transmitter to an adequate volume to alert the subject trainee. Additionally, upon sensing the wetness condition, the continuity detector enables the transmitter to begin transmitting. The output of the transmitter signal passes through the antenna coupler. From the antenna coupler, the transmitter output passes through a connector system to the electrodes of the sensor wick and conductor assembly, which can serve as the transmitter's antenna. In order to keep electrical consumption low, the transmitter may be preferably pulsed at a low duty cycle by a pulse oscillator. To increase the reliability of communication between the transmitter and the receiver, the radio frequency signal from the transmitter may be modulation encoded by the modulator according to the unique output code of an optional identity tone generator. The receiver may be programmed to respond only to a unique code.

BRIEF DESCRIPTION OF THE DRAWINGS

The invention, its configuration, construction, and operation will be best further described in the following detailed description, taken in conjunction with the accompanying drawings in which:

FIG. 1 is a plan view of a receiver which is utilizable in conjunction with the wetness awareness training device and system of the invention;

FIG. 2 is a perspective view of a diaper in a shape as it would assume while being worn by a user which is not shown in order to give a view of the front inside portion of the diaper from the vantage point of the rear of the diaper to illustrate a sensor/transmitter, sensor wick and conductor assembly and attachment member;

FIG. 5 is a plan view of the sensor wick and conductor assembly with a broken portion at the middle to illustrate that it can be of any length, including availability on a continuous roll;

FIG. 6 is an end sectional view of the sensor wick and conductor assembly illustrating two conductors mounted upon a wicking layer, an adhesive layer on the opposite side, and a release liner;

FIG. 7 is an end sectional view of a variation on the sensor wick and conductor assembly seen in FIG. 6 and illustrating two conductors mounted upon a wicking layer, with the wicking layer supported by a backing sheet, with the backing sheet having an adhesive layer on the opposite side, and a release liner;

FIG. 8 is an end sectional view of a variation on the sensor wick and conductor assembly seen in FIGS. 6 & 7 and illustrating two conductors mounted upon a wicking layer, which extends between and partially underneath the two conductors, and including with the wicking layer and conductors supported by a backing sheet, with the backing sheet having an adhesive layer on the opposite side, and a release liner;

FIG. 10 is a side view of the transmitter seen in FIG. 2 and illustrating the side of one of the two contact electrodes;

FIG. 11 is a rear view of the transmitter seen in FIGS. 2 and 10 and illustrating the two spaced apart contact electrodes;

FIG. 12 is a block diagram of one configuration of a receiver utilizable on conjunction with the wetness awareness training device and system of the invention;

DETAILED DESCRIPTION OF THE PREFERRED EMBODIMENT

Figure 4:
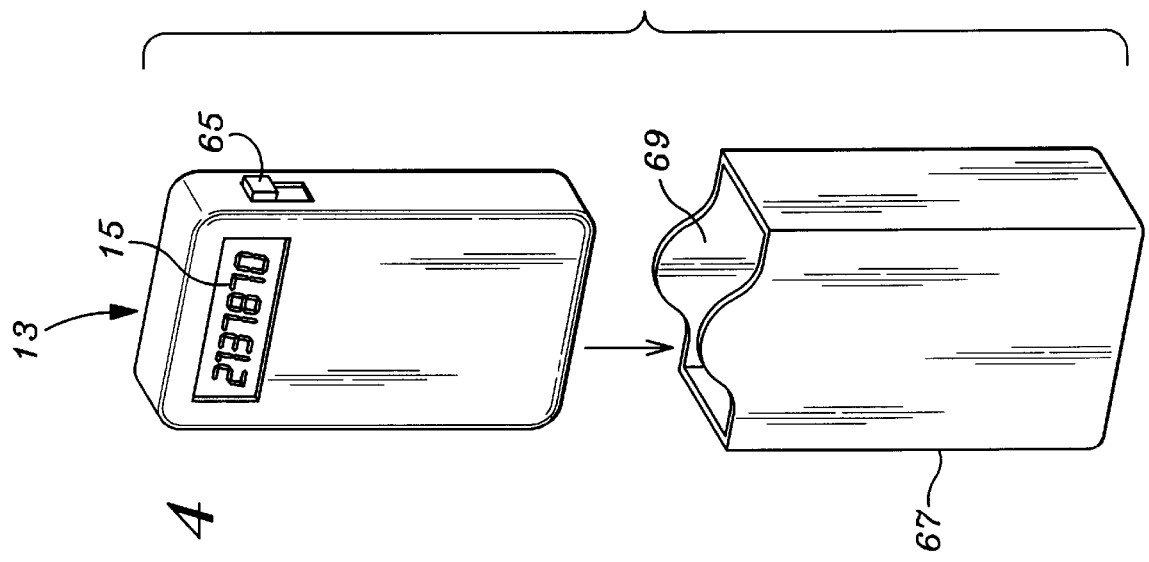
FIG. 4 is an exploded view of a holding case having an upper opening for receiving and carrying the receiver seen in FIG. 1.

The description and operation of the contained direct particle beam flow abrasion system of the present invention will be best described with reference to FIGS. 1 and 2. A wetness awareness training device and system is referred to with the numeral 11. In FIG. 1, a receiver 13 may have a readout window 15 and it may also have an internal antenna or an external antenna 17 shown schematically.

Referring to FIG. 2, a diaper structure 21 may have an upper body opening 23 with an upper rim edge 25. At a front center 27 of diaper structure 21, a sensor wick and conductor assembly 31 is seen extending generally vertically within the diaper structure 21. Ideally the sensor wick and conductor assembly 31 is mounted to extend down from the front center 27 of the diaper structure 21 to extend along the body split separating the gluteus maximus of the wearer, and extending along the bottom of the diaper structure 21 and as far forward as is practicable and comfortable for the child wearer of the diaper structure 21. The sensor wick and conductor assembly 31 can be available in an extended length roll in order to enable a custom length to be installed each time, and to enable a savings from the cost of cutting and packaging different individual lengths of sensor wick and conductor assembly 31.

The sensor wick and conductor assembly 31 crosses over the top of upper rim edge 25 of the diaper structure 21 and then across a sensor/transmitter 35 which may have an internal antenna or an external antenna schematically represented by the numeral 37. A pivoting clip can be used, but in a purely adhesive mode of support and holding, the sensor wick and conductor assembly 31 extends over sensor transmitter 35, then down its outside surface and back onto the diaper structure 21. This configuration presents a smooth look and feel to the wearer and helps to prevent manipulation of the sensor/transmitter 35 by the wearer. In the alternative, other structures may be used, including a clip, a split bodied housing, or a slot structure to capture the upper rim edge 25 of the diaper structure 21. The sensor wick and conductor assembly 31 includes a pair of conductors 41 and 43, shown in broken away section with an optional covering layer 44 shown lying against the inside of the diaper structure as it extends over the sensor/transmitter 35, which will be removed in the vicinity of the area in which it makes electrical contact with the sensor/transmitter 35. The conductors 41 and 43 lie adjacent a wicking layer 45 which is shown broken away for illustration purposes only and which will immediately absorb and widely distribute urine moisture into intimate contact with the surface of the conductors 41 and 43 which are adhered to the wicking layer 45. Note that the conductors 41 and 43 are disposed toward the diaper structure 21 and will be disposed toward the sensor wick and conductor assembly 31 as conductor assembly 31 extends over the sensor/transmitter 35. with respect to the wicking layer as the sensor wick and conductor assembly 31 extends over the upper rim edge 25. Covering layer 44 represents a variety of covering material which will be more fully explored below.

If urine wetness occurs along any segment length of the sensor wick and conductor assembly 31, the wicking layer 45 will act to immediately absorb and spread the urine between portions of the conductors 41 and 43 nearest the entrance of the urine. As such, the urine need not be distributed along the length of the sensor wick and conductor assembly 31. This mechanism gives an early and positive resistance change between the conductors 41 and 43 which enables the sensor/transmitter 35 to immediately transmit an indication of a wet condition to the receiver 13.

Figure 3:
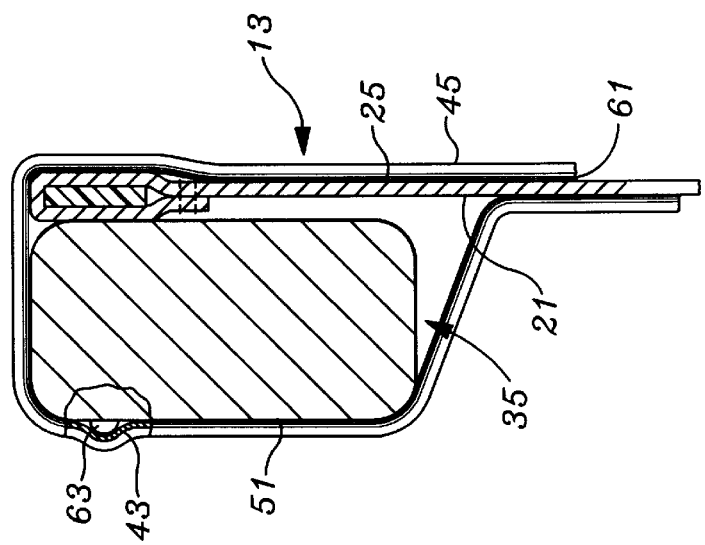
FIG. 3 is a side view taken along line 3—3 of FIG. 1 and illustrating how the sensor wick and conductor assembly folds over the diaper, and how one of two contacts on the body of the detector/transmitter engage the conductor electrodes in the sensor wick.

Referring to FIG. 3, a sectional view taken along line 3—3 of FIG. 2 illustrates the sensor/transmitter 35 of FIG. 2, as having a body 51 shown as a solid shape for illustrative purposes. FIG. 3 also illustrates a sectional view of the diaper structure 21 and the sensor wick and conductor assembly 31 which extends upwardly and over the upper end of the sensor wick and conductor assembly 31 and down over the back side of the sensor wick and conductor assembly 31. The sensor wick and conductor assembly 31 illustrated is shown with the adhesive carried directly by the wicking layer 45. Also seen between the diaper structure 21 and the sensor wick and conductor assembly 31 is a thin layer of adhesive 61 to cause the sensor wick and conductor assembly 31 to adhere to the diaper structure 21, and sensor wick and conductor assembly 31. A broken away section shows a contact 63 which contacts the conductor 43, just beyond the adhesive contact point, and is thus shown in section. As can be seen, the layer of adhesive 61 does not cover the conductors 43. Thus, the sensor/transmitter 35 is both grasped by the sensor wick and conductor assembly 31, secured to the diaper structure 21 by its adhesive surfaces, as well as served with conductive contact with the conductors 41 and 43. FIG. 3 illustrates that the sensor wick and conductor assembly 31 can continue on, completely around the sensor wick and conductor assembly 31 for attachment to the outside of the diaper structure 21 to provide added stability. The adhesive layer 61 may preferably not touch the contact 63, and may be configured to adhere the strip closely enough that good force of mechanical contact will be had so that the contact 63 will be in good electrical contact with its associated one of the conductors 41 and 43.

Referring to FIG. 4, a view of the receiver 13 seen in FIG. 1 which is seen as having the readout window 15 and an on/off switch 65. The receiver 13 is seen over a holding case 67 having an upper opening 69 through which the receiver 13 passes when it is supported. The holding case 67 can be of cloth, plastic or hard material, and it may or may not have other structures to enable it to be attached to the clothing of a care giver who desires to monitor wetness using the system 11 of the invention.

Referring to FIG. 5, a length of the sensor wick and conductor assembly 31 is seen, as are the conductors 41 and 43 attached thereto. The wicking layer 45 is seen and may constitute not only the material between the conductors 41 and 43, but also extending to the sides as far as the outer edges 71.

Referring to FIG. 6, a sectional view taken along line 6—6 of FIG. 5 illustrates a cross sectional view of the sensor wick and conductor assembly 31 as it exists prior to installation in a diaper structure 21. Conductors 41 and 43 are attached to one side of the wicking layer 45. Conductors 41 and 43 are spaced inwards from both sides 71 of the wicking layer 45. On the other side of the wicking layer is the adhesive layer 61. In FIG. 6 no additional structures are present and the wicking layer 45 extends to the full width, to edges 71. A release liner 75, typically made from paper waxed on one side, overlays and protects the adhesive layer 61 until the release liner 75 is removed. The conductors 41 and 43 are typically made from metal foil, may be bonded to the other side of the wicking layer 45.

Referring to FIG. 7, an alternative is shown in which the conductors 41 and 43 are supported by a wicking layer 45 and a cover layer 44 extending to the full width and out to the edges 71 of the sensor wick and conductor assembly 31, but an additional backing sheet 77 may be provided to support the cover layer 44 and their supported conductors 41 and 43. Conductors 41 and 43 are spaced inwards from both sides of the cover layer 44. When this structure is used, the thin layer of adhesive 61 is located on the other side of the backing sheet 77. Where the backing sheet 77 is present it is typically a soft, flexible, tear-resistant layer made out of plastic film.

Referring to FIG. 8, a further variation is shown where a wicking layer 45 extends underneath the conductors 41 and 43 and where the adhesive layer 61 is applied to the wicking layer 45, but where the conductors 41 and 43 are covered with the cover layer 44.

Figure 9:
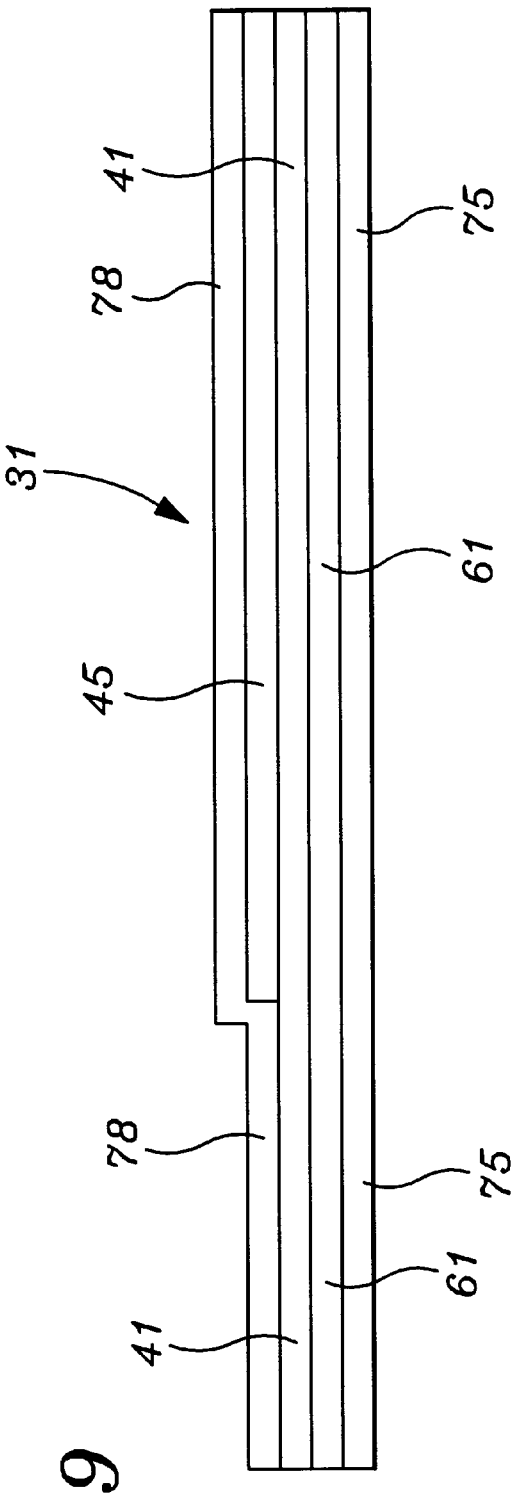
FIG. 9 is a side view of a variation in which the electrodes are covered in a lower section extending below a garment line, but where the upper portion of the sensor wick and conductor assembly is exposed for engagement by the sensor/transmitter.

Referring to FIG. 9, a two zone construction is illustrated, typically available in a fixed length embodiment of the sensor wick and conductor assembly 31. In this construction, the conductors 41 and 43, although only conductor 41 is seen, have the wicking layer 45 overlying the conductor 41. Overlying the wicking layer 45 is a porus, non-absorbing sheet 78. Because the sheet 78 and the wicking layer 45 both cover the conductors 41 and 43 only on one portion of the length of sensor wick and conductor assembly 31, the contacts 63 and 79 can contact the conductors 41 and 43 over a portion of the sensor wick and conductor assembly 31 once a release liner 75 is removed, the bare surfaces of the conductors 41 and 43 are available for electrical contact. Since FIG. 9 is a side profile, the adhesive layer 61 need not cover the conductors 41 and 43, but may cover the areas next to them. The adhesive layer 61 may be applied in a continuous stream on either side of and in between the conductors 41 and 43, without ever touching the conductors 41 and 43. In this event, even though not illustrated in FIG. 9, the adhesive layer 61 is also in contact with the wicking layer 45. Release liner 75 is used to expose the adhesive layer 61 for attachment to both the inside of the diaper structure as well as around the conductor assembly 31. The construction of FIG. 9 may not as amenable to continuous roll supply where the wicking layer 45 is provided as an abbreviated length layer. However, if the wicking layer 45 is extended completely to the end, such continuous roll supply would be possible.

Referring to FIG. 10, a side view of the sensor/transmitter 35 illustrates the position of a contact 79 which was not seen in FIG. 3 due to its mid sectional perspective. Referring to FIG. 11, the relative position of the contacts 63 and 79 is shown. The spacing of the contacts 63 and 79 correspond to the spacing of the conductors 41 and 43 so that the sensor/transmitter 35 lines up properly on the sensor wick and conductor assembly 31. The widths of the conductors 41 and 43 can be wider than as shown in the Figures to give a wider range of "bite" width of the sensor/transmitter 35 and contacts 63 and 79 may have with respect to the sensor wick and conductor assembly 31 as it is folded over the upper rim edge 25 of the diaper structure 21, and down along the outside of the sensor wick and conductor assembly 31. Also shown is an on/off slide switch 81 which can be used to turn the transmitter and sensor circuitry completely off during times when the child is asleep so that an audible noise, either from the sensor/transmitter 35 or from the receiver 13, will not wake the child. This can help the care giver to make a decision about the importance of sleep versus the importance of early notification on dryness. In addition, a child may be less likely to wet during sleep.

To ready the sensor wick and conductor assembly 31 for use a user removes and discards the release liner 75, and positions the sensor wick and conductor assembly 31 vertically on the inside of the inner portion of a garment which might be subject to urine wetness, including the diaper structure 21. The junction of the adhesive layer 61 of the backing sheet 77 if present, or the wicking layer 45 is pressed against the inside surface of the inner garment or diaper structure 21 until the sensor wick and conductor assembly 31 adheres to the garment. Enough of the sensor wick and conductor assembly 31 is left over at the top to fold down against a short portion of the outside of the garment. The short length folded down over the outside of the garment puts the conductors 41 and 43 in position to be engaged by the contacts 63 & 79 supported by the sensor/transmitter 35. Other types of contacts 63 & 79 may be used, including snaps, through material electrodes, and the like. The sensor/transmitter 35 is then placed against the outside of the garment, such as the diaper structure 21 at the upper rim edge 25 so that the exposed conductors 41 and 43 contact the contacts 63 and 79, respectively.

The system 11 is sensitive enough to immediately detect the initial presence of urine. The system 11 of the present invention incorporates a electrical continuity detector built into the sensor/transmitter 35 that reliably detects the level of conductivity in the sensor wick and conductor assembly 31 that corresponds to the act of urination. The sensor/transmitter 35 optionally utilizes an audible signaling device. This alarm is of such tone and volume to properly signal the subject trainee wearer upon the act of urination according to present thought and methods of a training system. Additionally, the sensor/transmitter contains a radio frequency transmitter that signals a remote Receiver carried by the care giver. The receiver 13 in the preferred embodiment is small enough in size and shape to allows it to be placed in a pocket or be attached to the clothing of the care giver. The receiver 13 is preferably battery powered, power consumption being low enough to allow infrequent changes of battery. Upon reception of the signal from the sensor/transmitter, the receiver 13 emits an audible beep tone to alert the care giver to the act of urination.

In order to increase the reliability of the radio communication process, the signal from the sensor/transmitter 35 may be encoded so that its signal is unique and can be differentiated from other radio frequency sources such as other transmitters including those of remote control devices, and electrical noise generated by household appliances. The receiver 13 may be programmed to respond only to this encoded signal, and emits an audible tone only when the received signal is properly encoded. In this way, the likelihood of false audible signals from the receiver 13 is greatly reduced.

Due to the small size of the sensor/transmitter 35 that is required for comfort, very little space is available in the unit for a battery to power the circuitry. Continuous radio transmission upon urination would quickly deplete the resource of the typical miniature battery. Instead of continuous transmission, the sensor/transmitter 35 is pulsed at a low duty cycle so that the power consumed is only a small fraction of what would be consumed for continuous radio transmission.

Referring to FIG. 12, one possible embodiment of a receiver 13 is seen. A battery 101 is attached to a connector system 103 and electrically connected to a power control relay block 105. Power control block 105 can supply power to other blocks, including those seen in FIG. 12 and may include a display, utility light, or status indication circuits and the like. The power control block 105 is also connected to a receiver block 107 shown with the schematic antenna 17. Power control 105 is also connected to a demodulator block 109, and the demodulator block 109 is optionally connected to an identity tone decoder 111. The identity tone decoder 111 is connected to a beep tone generator 113 which generates an tone signal to a speaker driver 115 which is in turn connected to a speaker 117. The speaker 117 alerts the care giver. Where no identity tone decoder 111 is present, the demodulator may be connected directly to the beep tone generator 113. The identity codes of the identity code decoder 111 and beep tones of the peep tone generator may be varied, as can the audio volume of the speaker driver.

Figure 13:
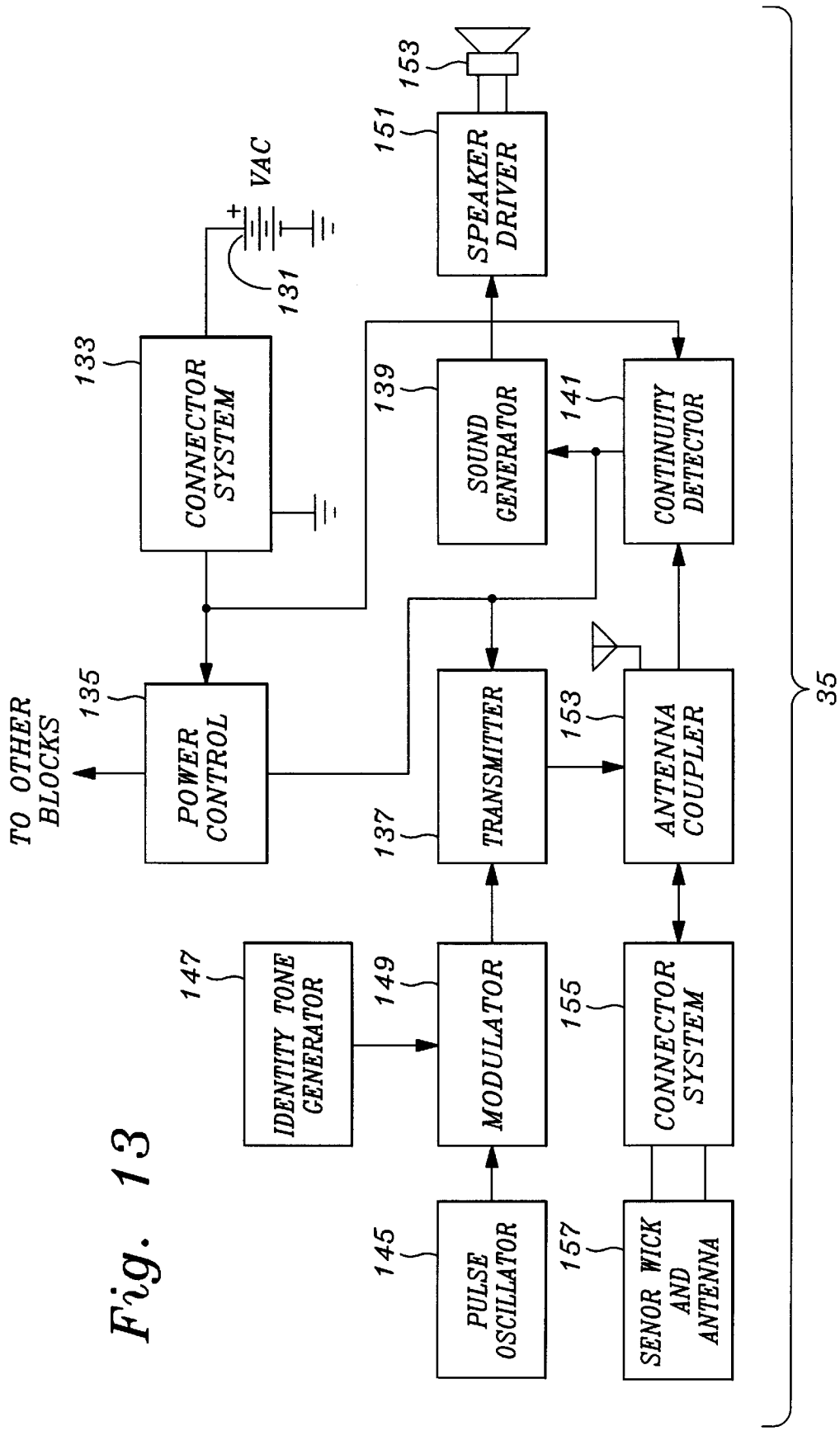
FIG. 13 is a block diagram of one embodiment of a sensor/transmitter circuit and optional speaker circuitry.

Referring to FIG. 13, a block diagram of one embodiment of a sensor/transmitter 35 is shown. A battery 131 is connected through a connector system 133 to supply power to a power control 135 for distribution to a transmitter 137, optional sound generator 139 and continuity detector 141, and to other blocks, including those shown in FIG. 13.

A pulse oscillator 145 and an identity tone generator 147 each connect their signals into a modulator 149. The modulator 149 is connected to the transmitter 137.

The optional sound generator 139 is connected to a speaker driver 151 which is, in turn, connected to a speaker 153.

The transmitter 137 is connected to an antenna coupler 153 which may be a simple connection to the contacts 63 and 79 or may be a more frequency specific coupler, such as capacitive coupling or a filtered coupling. Especially where the sensor wick and conductor assembly 31 is used as an antenna, the antenna coupler 153 is connected to the continuity detector 141, and the antenna coupler, is connected through a connector system 155 to a sensor wick and antenna 157 which may preferably be the sensor wick and conductor assembly 31 shown in the Figures.

Figure 14:
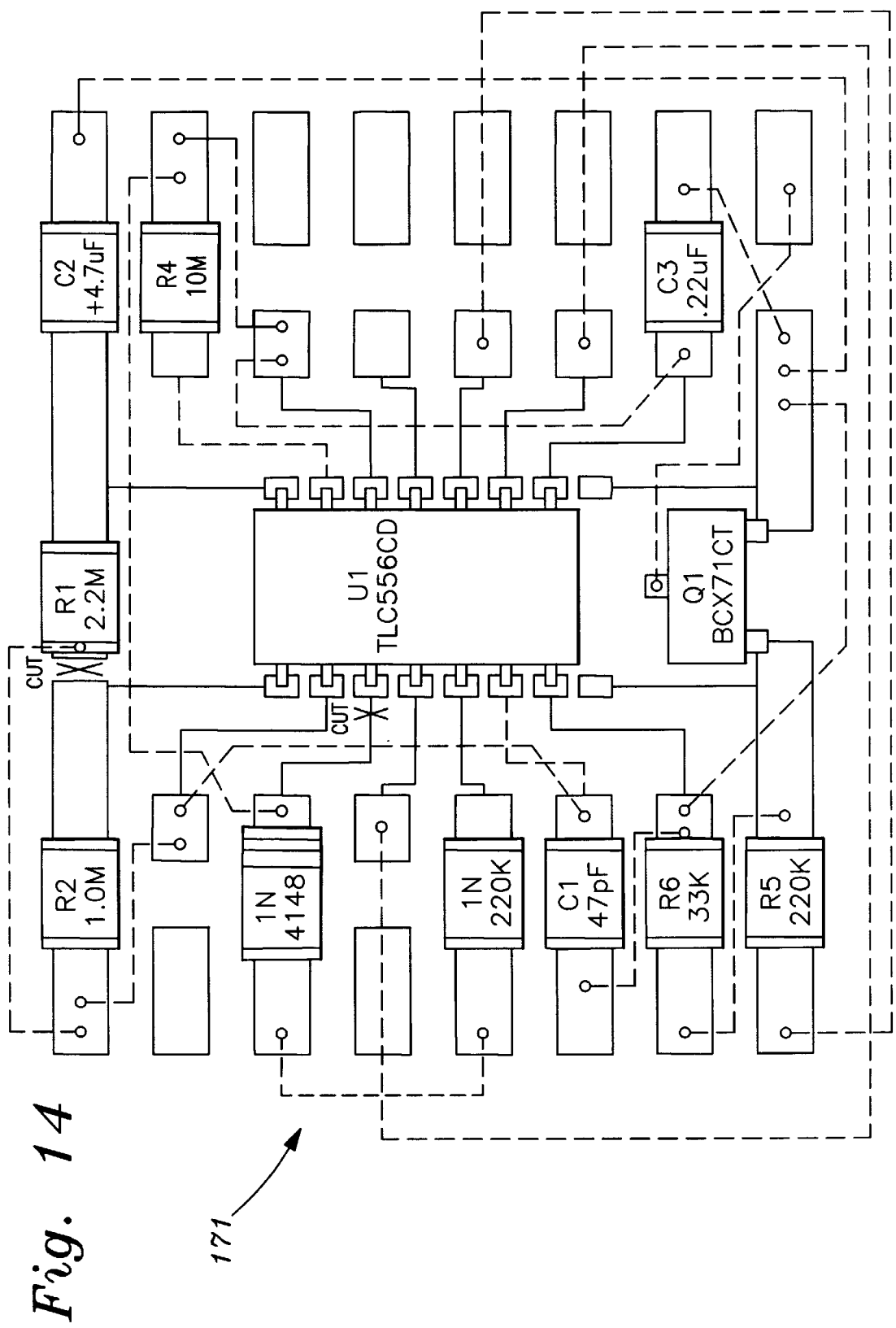
FIG. 14 is one embodiment of a microprocessor and surrounding circuitry utilizable in the transmitter of the wetness awareness training device and system of the invention.

Referring to FIG. 14, one embodiment of a sound generator is seen as a sound generator 171. A central microprocessor labeled U1TLC556CD is surrounded by the indicated resistors and capacitors which set the capabilities and frequency outputs which can include tones, codes and musical sequences. This sound generator circuit 171 can be used as either the beep tone generator 113 or as the sound generator 139.

While the present invention has been described in terms of a detector/transmitter and receiver monitoring system for detecting urine moisture in garments, one skilled in the art will realize that the structure and techniques of the present invention can be applied to many appliances including any appliance where a resistive indicator structure is to be combined with an antenna and where a triggering monitor is used as a precursor for energizing a transmitter in order to conserve energy.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A wetness awareness system comprising:
    an extended length layer of wicking material (45) having a first side and a second side;
    an extended length first conductor (41) and an extended length second conductor (43) spaced apart from said first conductor (41), said first and said second conductors (43) attached to said first side of said wicking material (45);
    an extended length layer of adhesive attached to said first side of said wicking material (45);
    a sensor/transmitter (35) having a first contact (63) for electrical connection with said first conductor (41) and a second contact (79) for electrical connection with said second conductor (43) as a portion of said extended length layer of wicking material (45) is aligned with said first and second contacts (63, 79), and for enabling said first and second contacts (63, 79) into contact with said first and second conductor (43)s, respectively, and including circuitry for detecting the resistance between said first and said second conductors (41, 43) when said wicking material (45) is wet and a transmitter for transmitting a signal indicating a wetness condition of said wicking material (45); and a receiver (13) for remotely receiving said signal indicating a wetness condition of said wicking material(45).

2. The wetness awareness system as recited in claim 1 wherein said sensor/transmitter (35) also contains a sound driver (115) and speaker (117) for alerting the wearer near a time at which said transmitting a signal indicating a wetness condition of said wicking material (45).

3. The wetness awareness system as recited in claim 2 wherein said sensor wick and conductor assembly further comprises an extended length layer of backing material interposed between said extended length layer of said wicking material (45) and said extended length layer of adhesive.

4. The wetness awareness system as recited in claim 1 and further comprising an extended length layer of porus, non-absorbing sheet directly overlying said extended length first conductor (41) and said extended length second conductor (43).

5. The wetness awareness system as recited in claim 1 wherein said sensor/transmitter (35) further comprises a housing (51) supporting said first and second contacts, attachable to clothing (21).

6. The wetness awareness system as recited in claim 5 wherein said sensor/transmitter (35) housing (51) supporting said first and second contacts, is attachable to clothing (21) by use of said extended length layer of wicking material (45).

7. The wetness awareness system as recited in claim 1 wherein said sensor/transmitter (35) further comprises:

a power supply (131);

a sensor circuit (141) powered by said power supply;

a power control (135) connected to said power supply (131); and a transmitter circuit (137) connected to said power control and configured to supply power to said transmitter circuit only after said sensor circuit detects said wetness condition of said wicking material (45).

8. The wetness awareness system as recited in claim 1 wherein said receiver further comprises a sound driver (115) and speaker (117) for alerting the wearer near a time at which said transmitting a signal indicating a wetness condition of said wicking material (45).

9. The wetness awareness system as recited in claim 1 and further comprising a covering layer (44) having a first side and a second side, said first side overlying a substantial part of said first and second conductors (41, 43) and said first side of said wicking material (45) and terminating short of contact of said first and second conductors (41, 43) with said first and second contacts (63, 79), respectively.

10. A transmitter sensor combination comprising:

a sensor for mounting inside a garment and having an extended length layer of wicking material (45) having a first side and a second side, and in contact with at least an extended length first conductor (41) and an extended length second conductor (43) spaced apart from said first conductor (41), said first and said second conductors (43) attached to said wicking material (45);

an extended length layer of adhesive attached to at least one of directly to and indirectly to said first side of said wicking material (45) to allow said extended length layer of wicking material to adhere to the inside surface of a garment, over an upper rim edge of said garment and partially along an outside surface of said garment forming a fold;

a sensor/transmitter (35) having a first contact (63) for electrical connection with said first conductor (41) and a second contact (79) for electrical connection with said second conductor (43) as a portion of said extended length layer of wicking material (45) is formed into a fold over said garment and aligned with said first and second contacts (63, 79), and for enabling said first and second contacts (63, 79) into contact with said first and second conductors (41,43), respectively, and for both mechanical and electrical engagement of said sensor/transmitter (35) with said extended length layer of wicking material (45) and said first and second conductors (41, 43), respectively, and including circuitry for detecting the resistance between said first and said second conductors (41, 43) when said wicking material (45) is wet and a transmitter for transmitting a signal indicating a wetness condition of said wicking material (45).

11. The transmitter sensor combination as recited in claim 10 wherein said fold of said extended length layer of wicking material (45) extends over said sensor/transmitter (35) for securing it to said garment.

12. The transmitter sensor combination as recited in claim 10 and further comprising an extended length layer of porus, non-absorbing sheet directly overlying said extended length first conductor (41) and said extended length second conductor (43).

13. The transmitter sensor combination as recited in claim 10 configured to enable said electrical engagement of said first and second contacts (63, 79) of said sensor/transmitter (35) with said first and second conductors (41, 43), respectively, away from said garment.

* * * * *